United States Patent [19]

Durfee

[11] Patent Number: 5,203,776
[45] Date of Patent: Apr. 20, 1993

[54] CATHETER

[76] Inventor: Paul J. Durfee, 3408 Mapleleaf La., Dallas, Tex. 75233

[21] Appl. No.: 959,295
[22] Filed: Oct. 9, 1992
[51] Int. Cl.$^5$ .............................................. A61M 5/00
[52] U.S. Cl. ................................... 604/264; 604/280; 604/281
[58] Field of Search ................ 604/264, 280, 281, 95, 604/96, 53, 282; 128/656, 657, 658

[56] References Cited

U.S. PATENT DOCUMENTS

| | | | |
|---|---|---|---|
| 3,935,857 | 2/1976 | Co | 604/280 X |
| 4,747,840 | 5/1988 | Ladika et al. | 604/280 X |
| 4,784,639 | 11/1988 | Patel | 604/53 |
| 4,822,345 | 4/1989 | Danforth | 604/282 |
| 4,886,506 | 12/1989 | Lovgren et al. | 604/96 X |
| 4,898,577 | 2/1990 | Badger et al. | 604/53 |
| 4,935,017 | 6/1990 | Sylvanowicz | 604/53 X |
| 5,044,369 | 9/1991 | Sahota | 604/96 X |
| 5,045,072 | 9/1991 | Castillo et al. | 604/280 |

FOREIGN PATENT DOCUMENTS 9200468 8/1992 PCT Int'l Appl. .

Primary Examiner—John D. Yasko
Attorney, Agent, or Firm—John M. Cone; William Lloyd Clayborn

[57] ABSTRACT

A catheter for insertion through a main artery into a branch artery ostium comprises a shaft, an integral profiled portion, and an integral tip portion. The profiled portion comprises a series of bends and straight legs. The tip portion of the catheter axially engages the branch artery. The profiled portion is shaped and dimensioned so that when the tip portion is engaged with the branch artery, the leg of the profiled portion adjacent to the shaft will be parallel to and engaged with the opposing inner wall of the main artery to resist forces tending to displace the tip portion from the branch artery.

5 Claims, 2 Drawing Sheets

CATHETER

BACKGROUND OF THE INVENTION

The present invention relates to the field of vascular catheters. More particularly, the present invention is related to a guide catheter which is adapted for insertion through a main artery into a branch artery ostium. Such catheters may be used to conduct a radio-opaque dye to the branch artery for diagnostic purposes, or for guiding a balloon catheter to a stenotic lesion in the branch artery for treatment purposes, such as in percutaneous transluminal coronary angioplasty.

In the case of the aorta, the coronary arteries which branch therefrom do so at angles approaching 90 degrees. The same can be said for the arteries of numerous other organs, such as renal and pulmonary arteries. A number of guide catheters having curved distal portions have been developed to facilitate engaging the ostia of such arteries. The Judkins, Amplatz, and Gamal guide catheters are examples of curves which are presently available.

In conventional coronary angioplasty procedure, a wire inserted into the guide catheter from the catheter's proximal end to its distal end straightens the curved portion of the catheter. The distal end of the catheter is then inserted into the patient's right femoral artery or, occasionally, the patient's right brachial artery, left brachial artery, or left femoral artery. The guide catheter and wire are then pushed up the artery and into the aorta until the distal end of the catheter is adjacent to the desired branch artery. The wire is withdrawn and the distal end of the catheter is maneuvered to engage the ostium of the branch artery.

After the guide catheter is positioned to engage the branch artery ostium, a balloon catheter is passed through the guide catheter and into the branch artery. The balloon portion of the balloon catheter is then maneuvered into position within the stenotic lesion and inflated to compact and split the material of the lesion, thereby increasing the diameter of the lumen through the lesion to facilitate the flow of blood through it. To enable the balloon catheter to be maneuvered into position, a guide wire may be attached to the distal end of the balloon catheter or passed through a lumen within the balloon catheter.

The guide catheter curves which are presently available have a tendency to engage the wall of the branch artery ostium and are easily dislodged from the ostium. FIGS. 1 and 2 show a catheter 1 having a Judkins left curve engaging the ostium 3 of the left main coronary artery 5. The Judkins curve extends from the point designated by reference number 7 to the tip 9 of the catheter 1.

As best seen in FIG. 2, the tip 9 of the catheter 1 engages an upper wall 11 of the artery 5 adjacent to the ostium 3. Engagement in this manner causes several problems. The tip 9 of the catheter 1 may cause trauma to the wall 11 of the artery 5 at the point of contact 13. In addition, the distal portion of the catheter 1 restricts the flow of blood from the aorta 15 into the artery 5, which may cause trauma to the portions of the heart supplied by the artery 5. Finally, when a balloon catheter 17 is passed through the catheter 1, the catheter 17 will contact the upper wall 11 of the artery 5, causing an area of friction 19. A force resulting from the area of friction 19, which the direction of is indicated by the arrow at reference number 21, tends to push the tip 9 out of the ostium 3 of the branch artery 5.

In many cases, the stenotic lesion (not shown) to be treated very nearly occludes the artery (not shown) in which it is located. Thus, the surgeon performing the angioplasty may meet with considerable resistance as he or she attempts to introduce the balloon catheter 17 into the lesion. A force resulting from overcoming that resistance also acts in the direction 21.

As best seen in FIG. 1 a force in direction 21, acting on the lever arm formed by the portion of the catheter 1 between an apex 23 and a lower bend 25, tends to bend the catheter 1 about the apex 23. As a result, the tip 9 of the catheter 1 is frequently disengaged from the ostium 3 of the artery 5. If this occurs before the balloon catheter 17 is properly positioned, the balloon catheter 17 and the catheter 1 may have to be withdrawn from the patient and the procedure begun again.

To avoid disengagement of the tip 9 of the catheter 1 from the ostium 3 of the artery 5, the catheter 1 may be maneuvered to extend further into the artery 5. While such extension decreases the tendency of the catheter 1 to disengage from the artery 5, it increases the possibility of causing trauma to the artery 9 and may cause the artery 9 to spasm.

SUMMARY OF THE INVENTION

An object of the present invention is to provide a catheter for insertion through a main artery into a branch artery ostium which resists disengagement of its distal end from the branch artery. A further object is to provide a catheter which minimizes restriction of blood flow into the branch artery. A still further object is to provide a catheter which minimizes the possibility of trauma to the wall of the branch artery.

The present invention provides a catheter for insertion through a main artery into a branch artery ostium, which catheter comprises a tubular member comprising a shaft, an integral profiled portion, and an integral, substantially straight tip portion. The tip portion is adapted to axially engage the branch artery through the branch artery ostium. Advantageously, the axial engagement minimizes the catheter's restriction of blood flow to the branch artery and minimizes the possibility of the catheter causing trauma to the inner wall of the branch artery.

The profiled portion connects the shaft to the tip portion and is comprised of three bends and two substantially straight legs. When the tip portion is engaged with the branch artery, a first leg (the leg adjacent to the shaft) is disposed adjacent to and substantially parallel to the opposing inner wall of the main artery. Advantageously, when a force is applied to the tip portion of the catheter, the force is transmitted to the first leg and is substantially dissipated by the bends between the tip portion and the first leg, and by the interaction of the first leg with the inner wall of the main artery. Thus, movement of the tip portion is minimized. A further advantage is that the profiled portion provides a shorter moment arm for the force to act upon than in the present curves, decreasing the bending moment applied to the catheter of the present invention, which further minimizes movement of the tip portion.

BRIEF DESCRIPTION OF THE DRAWINGS

An embodiment of the invention will be described, by way of example only, with reference to the accompanying drawings, in which.

DETAILED DESCRIPTION

Figure 3:
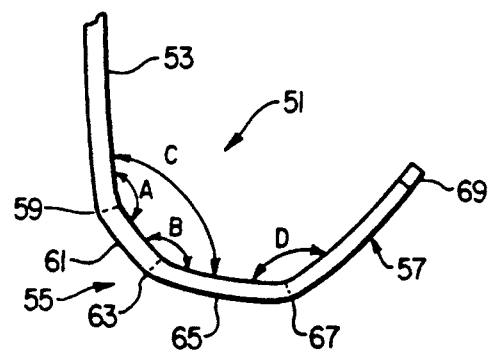
FIG. 3 is a side view of the distal portion of an embodiment of the present invention.

Referring to FIG. 3, a catheter 51 comprises a shaft 53, an integral profiled portion 55, and an integral tip portion 57. A majority of the length of the shaft 53 has been omitted.

The profiled portion 55 of the catheter 51 extends from the distal end of the shaft 53 to the proximal end of the tip portion 57 and is comprised of a first bend 59, a first substantially straight leg 61, a second bend 63, a second substantially straight leg 65, and a third bend 67. The angle A of the first bend 61 is between about 145 and about 155 degrees. The angle B of the second bend 63 is between about 135 and about 145 degrees. Thus, the angle C between the shaft 53 and the second leg 65 is between about 100 and about 120 degrees. The angle D of the third bend 67 is between about 100 and about 135 degrees.

Measured axially, the first leg 61 is about 1 cm in length and the second leg 65 is about 2 cm in length. Including the length of the bends 59, 63, and 67, the profiled portion 55 of the catheter 51 is about 4 to 5 cm in length.

The tip portion 57 may be about 0.75, 1.25, 2.5, or 3 cm long. As a result of the different lengths of the tip portion 57, the catheter 51 may be used to engage the ostia of the left main and right coronary arteries, as well as the ostia of saphenous vein grafts, in hearts of varying size. Thus, this embodiment of the invention provides a complete system of catheters for coronary angioplasty and angiography.

In this embodiment of the invention, the shaft 53 is constructed of a stainless steel wire mesh, an outer sheath of polyurethane, and an inner lining of a low-friction synthetic resin polymer, such as "Teflon". The profiled portion 55 and tip portion 57 of the catheter 51 are constructed of polyurethane with a low-friction liner. This construction provides a catheter 51 which is relatively stiff axially and torsionally, somewhat less stiff laterally, and has low-friction inner and outer surfaces. The catheter 51 may be constructed of other materials which provide the foregoing characteristics. For instance, the catheter 51 could be made entirely of polyurethane.

A distal tip 69 of the catheter 51 is made of a soft material, such as soft nylon, to minimize the possibility of causing trauma to the inner walls of the arteries with which the tip 69 comes into contact.

Figure 1:
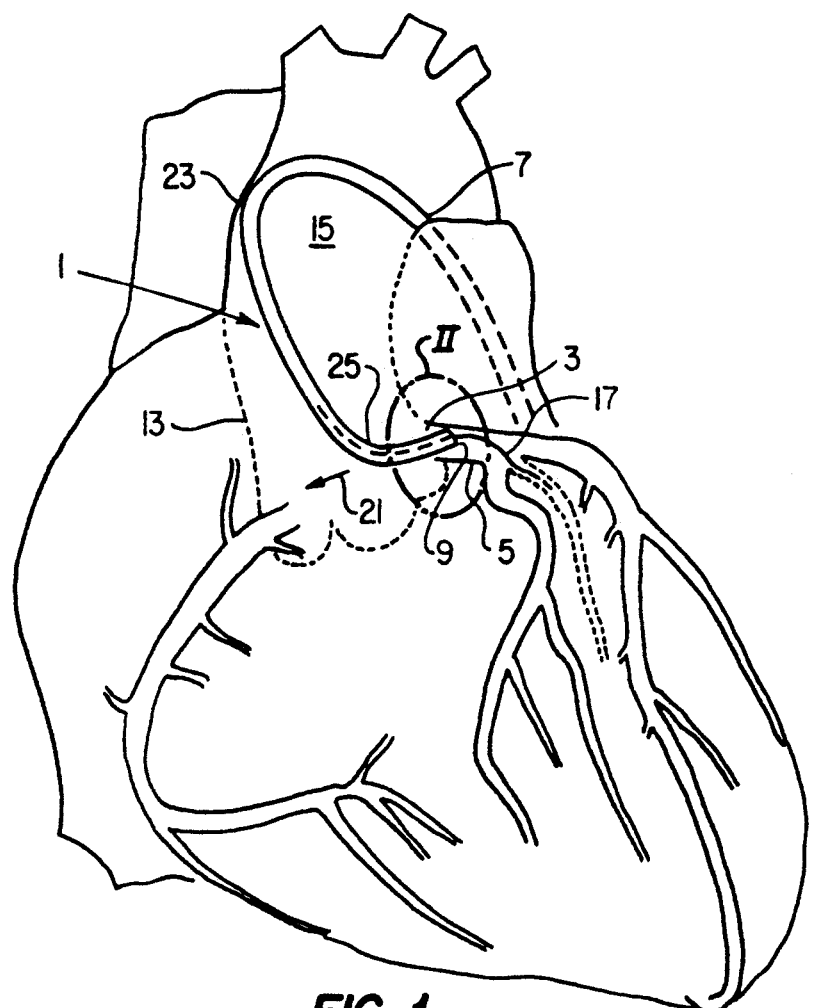
FIG. 1 is a partially cutaway view of a heart having inserted therein a prior art catheter.
Figure 2:
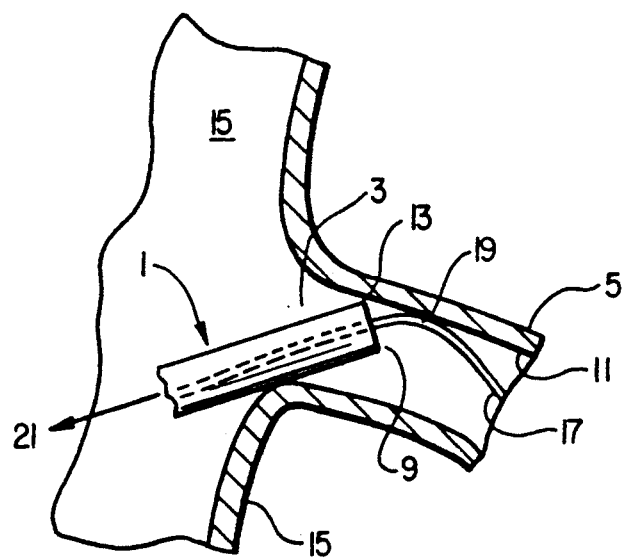
FIG. 2 is an enlarged view of area II in FIG. 1.
Figure 4:
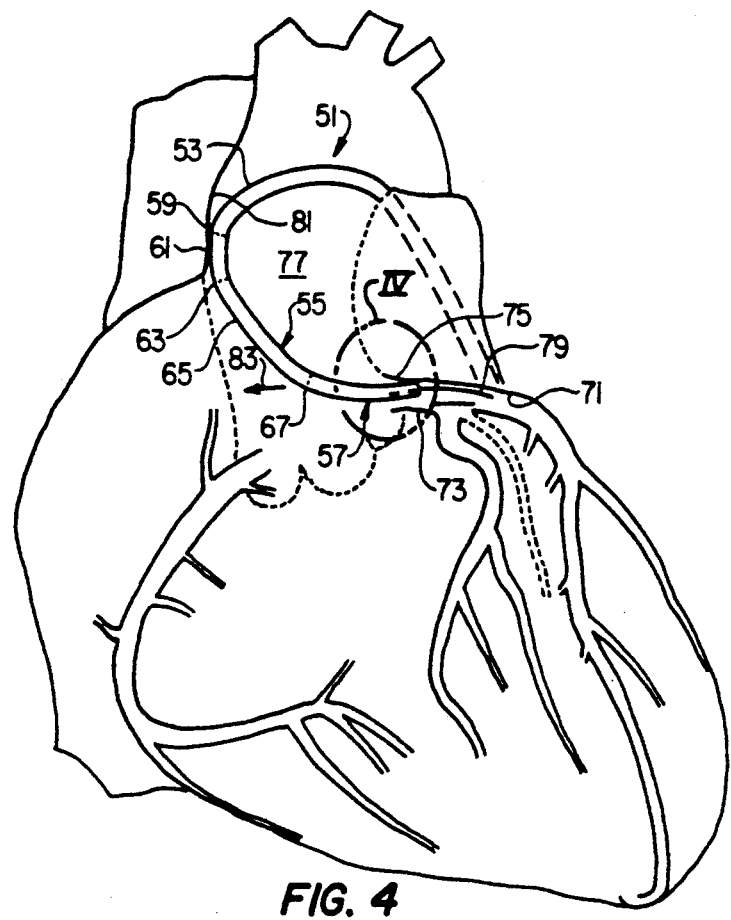
FIG. 4 is partially cutaway view of a heart having inserted therein an embodiment of the present invention.
Figure 5:
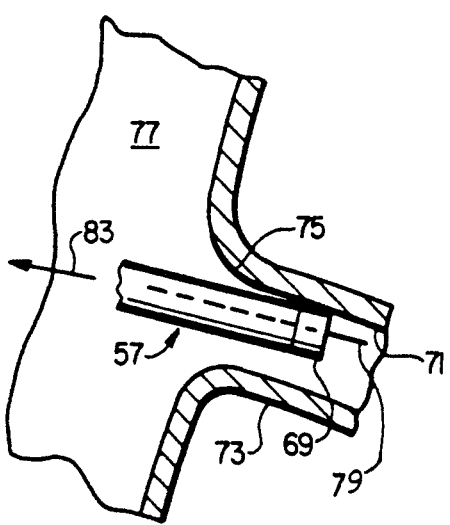
FIG. 5 is an enlarged view of area IV in FIG. 3.

In FIGS. 4 and 5, the distal end of the tip portion 57 of the catheter 51 axially engages an inner wall 71 of the left main coronary artery 73. This axial alignment provides several advantages:

First, the tip portion 57 of the catheter 51 extends beyond the ostium 75 into the artery 73, so that the tip portion 57 must move a greater distance before it becomes disengaged from the ostium 75;

Second, restriction of blood flow from the aorta 77 to the artery 73 is minimized;

Third, the tip portion 57 of the catheter 51 contacts the inner wall 71 of the artery 73 over an area rather than substantially at a point as in the case of prior art catheters (see FIGS. 1 and 2); and Fourth, when a balloon catheter 79 is passed through the catheter 51, the balloon catheter 79 either does not contact the inner wall 71 of the artery 73 or contacts the inner wall 71 at a smaller angle than is the case with prior art catheters, resulting in a smaller frictional force acting to disengage the tip portion 57 of the catheter 51 from the ostium 75 of the artery 73.

A force 83 may result from frictional interaction between the balloon catheter 79 and the inner wall 71 of the artery 73 and from resistance of a stenotic lesion (not shown) to the insertion of the balloon catheter 79. The force 83 tends to push the tip portion 57 of the catheter 51 out of the ostium 75 of the artery 73. As can be seen in FIG. 4, when the tip portion 57 of the catheter 51 is engaged within the artery 73, the first leg 61 engages an inner opposed wall 81 of the aorta 77. The force 83 is transferred from the tip portion 57 through the profiled portion 55 to the shaft 53. The inner wall 81 of the aorta 77 absorbs a major portion of the force 83 from the first leg 61 while allowing relatively small movement of the tip portion 79 of the catheter 51. Substantially all of the remainder of the force 83 is absorbed by the bends 59, 61, and 63 as the force 83 is transferred along the profiled portion 55 of the catheter 51. The moment arm (from the third bend 67 to the first bend 59) on which the force 83 acts is shorter than that for prior art catheters (see FIG. 1), which results in smaller bending moments being applied to the bends 59, 61, and 63. Thus, for a given magnitude of force 83, the tip portion 57 of the catheter 51 embodying the present invention will move substantially less with prior art catheters, resulting in the tip portion 57 remaining engaged within the ostia 75 of the artery 73.

While the preferred embodiment of the invention has been shown and described, it will be apparent to those skilled in this art that various modifications may be made to this embodiment without departing from the spirit of the present invention. For that reason, the scope of the invention is set forth in the following claims.

I claim:

1. A catheter for insertion through an aorta into a coronary artery, said catheter comprising:

a tubular member comprising a shaft, an integral profiled portion, and an integral, substantially straight tip portion;

said tip portion being adapted to axially engage said coronary artery;

said profiled portion comprising, in order from said shaft portion to said tip portion, a first bend, a first substantially straight leg, a second bend, a second substantially straight leg, and a third bend;

said shaft and said second leg being disposed relative to each other at an angle between about 100 to about 120 degrees;

said first leg being about 1 cm in length;

said second leg being about 2 cm in length; and said profiled portion being about 4 to about 5 cm in length, including said bends;

whereby when said tip portion is engaged with said coronary artery, said first leg will be approximately parallel to an engaged with an opposing inner wall of the aorta to resist forces tending to displace said tip portion from said coronary artery.

2. The catheter of claim 1 wherein said tip portion is between about 0.75 to about 3 cm in length to enable said tip portion to engage all coronary arteries and grafts which branch from said aorta and to accommodate different size hearts.

3. The catheter of claim 1 wherein said second leg and said tip portion are disposed relative to each other at an angle between about 110 to about 135 degrees.

4. A catheter for insertion through an aorta into a branch artery, said catheter comprising:
- a tubular member comprising a shaft, an integral profiled portion, and an integral, substantially straight tip portion;
- said tip portion being adapted to axially engage said branch artery;
- said profiled portion comprising, in order from said shaft portion to said tip portion, a first bend, a first substantially straight leg, a second bend, a second substantially straight leg, and a third bend;
- said profiled portion being shaped and dimensioned so that when said tip portion is engaged with said branch artery, said first leg will be parallel to and engaged with an opposing inner wall of the aorta to resist forces tending to displace said tip portion from said branch artery.

5. The catheter of claim 4 wherein said shaft and said second leg are disposed relative to each other at an angle between about 100 to about 120 degrees.

* * * * *

UNITED STATES PATENT AND TRADEMARK OFFICE
CERTIFICATE OF CORRECTION

PATENT NO. : 5,203,776
DATED : April 20, 1993
INVENTOR(S) : Paul J. Durfee

It is certified that error appears in the above-indentified patent and that said Letters Patent is hereby corrected as shown below:

At column 4 line 66, change "an engaged" to -- and engaged --.

Signed and Sealed this

Twenty-fifth Day of January, 1994

Attest:

BRUCE LEHMAN

Attesting Officer

Commissioner of Patents and Trademarks